United States Patent

Käsbauer et al.

Patent Number: 5,096,625
Date of Patent: Mar. 17, 1992

[54] PROCESS FOR THE SULPHOXIDATION OF N-PARAFFINS

[75] Inventors: Josef Käsbauer, Wermelskirchen; Helmut Fiege, Leverkusen, both of Fed. Rep. of Germany

[73] Assignee: Bayer Aktiengesellschaft, Leverkusen, Fed. Rep. of Germany

[21] Appl. No.: 591,659

[22] Filed: Oct. 2, 1990

[30] Foreign Application Priority Data

Oct. 26, 1989 [DE] Fed. Rep. of Germany ....... 3935642

[51] Int. Cl.$^5$ ................................................. C11C 1/04
[52] U.S. Cl. ..................................... 260/416; 562/121
[58] Field of Search ......................... 260/416; 562/121

[56] References Cited

U.S. PATENT DOCUMENTS 3,660,471  5/1972  Sawano et al. ...................... 562/121
3,666,797  5/1972  Nagayama et al.

Primary Examiner—Jose G. Dees
Assistant Examiner—Deborah D. Carr
Attorney, Agent, or Firm—Sprung, Horn, Kramer & Woods

[57] ABSTRACT

Aliphatic sulphonic acids can be prepared by reacting n-paraffins with $SO_2$ and $O_2$ under UV irradiation with high selectivity even at conversions of up to 12 mol % if an amount of water is added which is appropriate to ensure that after the reaction has commenced and the stationary state has been reached, the sulphoxidation proceeds in homogeneous phase.

7 Claims, No Drawings

PROCESS FOR THE SULPHOXIDATION OF N-PARAFFINS

BACKGROUND OF THE INVENTION

The present invention relates to a novel process for the sulphoxidation of n-paraffins using sulphur dioxide and oxygen under irradiation with UV-containing light in the presence of an amount of water which is appropriate to ensure that the sulphoxidation mixture is in homogeneous phase.

Among the various process variants for the sulphoxidation of n-paraffins, the most advantageous from the points of view of economy and quality is the so-called light-water process (Chemie in unserer Zeit 13 (1979), 157). The addition of water allows the paraffinpersulphonic acid which is produced as an intermediate to react with sulphur dioxide giving paraffinsulphonic acid and sulphuric acid. The amount of water added is normally appropriate to ensure that a two-phase system is present during the sulphoxidation.

DE-C-910,165 discloses a further variant of the sulphoxidation with water addition, in which paraffin and water are emulsified by means of a very high throughput of the reaction gases. However, in this variant, the water is not ideally distributed. This has a deleterious effect on the undesired formation of paraffindisulphonic acid which, for quality reasons, must be limited to 10% by weight. This limitation allows only a very low parafin conversion with disadvantages with regard to space-time yield. In this respect, H. G. Hauthal, Alkanesulfonates (1985) mentions a conversion of 1%. The previously cited DE-A-910,165 mentions a conversion of about 0.6%, and EP 282,962 mentions a figure of about 1.5%.

DE-C-910,165 and DE-B-1,910,860 refer to the amount of water added. According to these documents, the amount of water added to the reaction mixture must be determined in such a way that the concentration of the resulting sulphuric acid in the aqueous phase does not increase beyond 20%; no justification for this statement is given in the abovementioned documents.

The object of the invention is therefore to provide a process for the sulphoxidation of n-paraffins using sulphur dioxide and oxygen under UV-irradiation and with the addition of water, in which the reaction gives paraffinsulphonic acid with high selectivity under industrially more favourable conditions and also at higher conversion.

Surprisingly, in the sulphoxidation, a very narrow, conversion-dependent range of water concentration has been found within which the sulphoxidation mixture is present in the form of a water-white, homogeneous reaction solution. Advantageously, within this range, paraffin is converted to paraffinsulphonic acid with high selectivity at significantly higher conversion.

SUMMARY OF THE INVENTION

Accordingly, a process has been found for the preparation of aliphatic sulphonic acids by reacting n-paraffins with sulphur dioxide and oxygen in the presence of water and under irradiation by UV-containing light (sulphoxidation), which is characterized in that the sulphoxidation is carried out in homogeneous phase after the reaction has commenced and the stationary state has been reached.

DETAILED DESCRIPTION OF THE INVENTION

Obviously, it is possible empirically to determine the amount of water which is to be added in total to the reaction mixture as the paraffin conversion proceeds in order to maintain the necessary homogeneous phase according to the invention. However, it is preferable to calculate the amount of water added in each case from the paraffin conversion achieved in each case using the formula $$H_2O[\% \text{ by weight}] = \text{paraffin conversion[mol \%]} \times 0.93 + (1.67 \pm 0.5),$$

the terms used in the equation being the total amount of water added in each case to the reaction mixture in percent by weight relative to the weight of paraffin present at the start of the reaction and the total weight of added water, and the paraffin conversion in mol %, relative to the weight of paraffin present at the start of the reaction.

This formula for maintaining the homogeneous phase is valid after the reaction has commenced and the stationary state has been reached.

The paraffin conversion is calculated from the oxygen consumption, i.e. from the difference between the oxygen introduced into the reaction mixture and the oxygen determined in the off-gas. To comply with a specification limiting the paraffindisulphonic acid to a maximum of 10% by weight, the process according to the invention is preferably carried out within a conversion range of 0.5 to 12 mol %, relative to the weight of paraffin present at the start of the reaction. Preferably, the process according to the invention is carried out within a conversion range of 2.5 to 10 mol %.

At the start of the reaction, the process according to the invention can be begun using a somewhat higher water content than that corresponding to the abovementioned formula, for example using an amount of 1.17 to 5% by weight of water, which is initially charged or is present in the reaction mixture at the start of the reaction. Preferably, 1.17 to 4% by weight of water are initially charged or are present in the reaction mixture at the start. In the further course of the process according to the invention, for example from a conversion of 1 mol %, preferably from 1.5 mol %, but at the latest from 3 mol %, the reaction path enters a stationary state in homogeneous phase and once this stationary state has been reached, the reaction is conducted further in accordance with the above formula.

Controlling the amount of water to achieve the total amount of added water required in accordance with the abovementioned formula is achieved in the above-mentioned manner via the amount of oxygen which has been consumed during the reaction and which is equivalent to the amount of paraffin which has been converted. The sulphur dioxide which is also needed for the conversion dissolves readily in the reaction mixture. It is present in a slight excess, relative to the amount of oxygen consumed, for example in an excess of 1 to 20 mol %. Any excess $SO_2$ is not removed from this mixture until the reaction mixture is worked up and on removal can be collected in a suitable manner and recycled. Consequently, a mode of operation is achieved in the reactor which virtually eliminates off-gas, or a mode of operation without any off-gas requiring disposal.

The oxygen for the process according to the invention can be pure oxygen. It is possible to operate the process according to the invention so that the added oxygen is virtually completely consumed, a slight persistence of oxygen on the off-gas side being necessary only for the reliable determination of the oxygen consumption, this allowing the measurements required for controlling the water addition. Preferably however, owing to the absence of $SO_2$ from the off-gas, oxygen may also be used in the form of atmospheric air. This variant which is preferred owing to economy then gives an off-gas composed of nitrogen with only very small amounts of residual oxygen. This variant has the additional advantage of dispensing with safety measures which are necessary when working with pure oxygen. Obviously, the atmospheric air can be enriched with pure oxygen, for example until the safety limits are reached.

The reaction temperature is in the range from 30° to 40° C., which is known to a person skilled in the art.

The process according to the invention can be carried out advantageously as a continuous process.

The advantages of the process according to the invention are firstly the high selectivity even in a conversion range of above 5 mol %. Furthermore, the industrial practicality is improved since no stirring energy or mixing energy is required for the formation and maintenance of an oil/water emulsion. This allows the concentration of sulphur dioxide and oxygen for absorption to be reduced to such an extent, and to be adjusted in the presence of other mixing elements, for example of a simple stirrer, so that in the abovementioned manner, no off-gas requiring disposal, in particular no sulphur dioxide-containing off-gas results. The homogeneous, water-white reaction solution contains the water which has been added progressively in the course of the progress of the reaction in accordance with the above formula in an ideally distributed state and in a significantly lower amount than hitherto used. This significantly promotes the irradiation with UV-containing light.

The homogeneous, water-white and colourless reaction solution is worked up by adding sufficient water to give a two phase system. The phase separation is spontaneous and mull-free owing to the pronounced suppression of by-products. The aqueous phase from this phase separation is removed and is worked up in a manner known to a person skilled in the art. The paraffin phase from this phase separation can be directly reused without intermediate purification.

EXAMPLE 1

A 700 ml photolysis apparatus was initially charged with 425 g of n-paraffin ($C_{13}$–$C_{18}$ fraction) at 35° C. 17.7 g of water were added and, under irradiation from a 50 W low pressure Hg lamp, 1.26 g per hour of oxygen and 5.84 g per hour of sulphur dioxide were introduced with stirring and without off-gas being generated. After about 1.5 hours, the emulsion of the liquid reaction components became converted into a water-white, homogeneous solution. This homogeneous solution was maintained by pumping in 9.9 g per hour of water. After 5 hours, the sulphoxidation was terminated at a conversion of 10 mol %. The addition of 28.6 g of water gave a spontaneous mull-free phase separation into 290 g of paraffin phase and 234 g of aqueous phase. The colourless aqueous phase contained 21.63% of paraffinsulphonic acid and 1.92% of paraffindisulphonic acid, the latter corresponding to 8.15% by weight relative to the total amount of sulphonic acid material.

EXAMPLE 2

In a manner similar to that of Example 1, 4.66 g per hour of air and 5.7 g per hour of sulphur dioxide were introduced. After about 1.5 hours, 6.1 g per hour of water were pumped in. After 5.8 hours, the paraffin conversion was 8.5%. 90% of the atmospheric oxygen had reacted. The addition of 34.6 g of water gave a colourless aqueous phase which contained 20.6% of paraffinsulphonic acid and 0.7% of paraffindisulphonic acid (3.3% of the total amount of sulphonic acid material).

EXAMPLE 3 (COMPARATIVE EXAMPLE)

In a manner similar to that of Example 1, the starting components were treated in the course of 5.4 hours with 1.18 g per hour of oxygen and 5.46 g per hour of sulphur dioxide. However, after reaching the homogeneous phase, no further water was pumped in. The reaction solution became turbid and increasingly yellow in colour. At the end of the sulphoxidation, at a paraffin conversion of 10.8%, the addition of water gave a gel-like mass which only slowly separated into two phases. The yellow-coloured aqueous phase contained, besides 23.57% of paraffinsulphonic acid, 2.84% of paraffin disulphonic acid, the latter corresponding to 10.75% by weight relative to the total amount of sulphonic acid material.

What is claimed is:

1. A process for the preparation of aliphatic sulphonic acids by reacting n-paraffins with sulphur dioxide and oxygen in the presence of water and under irradiation by UV-containing light (sulphoxidation), wherein the sulphoxidation is carried out in homogeneous phase
wherein after the stationary state has been reached, the homogeneous phase is maintained using the content of water added in each case to the reaction mixture relative to the weight of paraffin present at the start of the reaction and the total added water, as a function of the paraffin conversion, the paraffin conversion being measured by the oxygen consumption, and the amount of water added in each case being linked to the paraffin conversion in mol % which has been achieved in each case, relative to the weight of paraffin present at the start, by the formula $$H_2O[\% \text{ by weight}] = \text{Paraffin conversion[mol \%]} \times 0.93 + (1.67 \pm 0.5);$$

and wherein the reaction is carried out within a conversion range of 0.5 to 12 mol %;
and wherein at the start of the reaction and until the stationary state has been reached, 1.17 to 5% by weight of water are initially charged or are present in the reaction mixture;
and wherein the reaction is carried out at 30° to 40° C.

2. The process of claim 1, wherein the reaction is carried out within a conversion range of 2.5 to 10 mol %.

3. The process of claim 1, wherein 1.17 to 4% by weight of water are initially charged or are present in the reaction mixture.

4. The process of claim 1, wherein the oxygen used is in the form of atmospheric air.

5. The process of claim 1, wherein in the course of the process from a conversion of 1 mol % the reaction is conducted further in accordance with the conversion of 1 mol % the reaction is conducted further in accordance with the formula of claim 4.

6. The process of claim 5, wherein from a conversion of 1.5 mol % the reaction is conducted in accordance with the formula of claim 4.

7. The process of claim 6, wherein from a conversion of 3 mol % the reaction is conducted in accordance with the formula of claim 4.

* * * * *

UNITED STATES PATENT AND TRADEMARK OFFICE
CERTIFICATE OF CORRECTION

PATENT NO. : 5,096,625

DATED : March 17, 1992

INVENTOR(S) : Kasbauer et al.

It is certified that error appears in the above-identified patent and that said Letters Patent is hereby corrected as shown below:

Col. 5, line 5    Delete " claim 4 " and substitute -- claim 2 --

Col. 6, lines 2 &  Delete " claim 4 " and substitute -- claim 2 --

Signed and Sealed this

Seventh Day of September, 1993

Attest:

BRUCE LEHMAN

Attesting Officer    Commissioner of Patents and Trademarks